United States Patent [19]

Stern et al.

[11] Patent Number: 5,370,989
[45] Date of Patent: Dec. 6, 1994

[54] SOLUTION FOR PROLONGED ORGAN PRESERVATION

[75] Inventors: David M. Stern, Great Neck, N.Y.; Mehmet C. Oz, Fort Lee; Roman Nowygrod, Teaneck, both of N.J.; Shin Koga, New York; David J. Pinsky, Riverdale, both of N.Y.

[73] Assignee: The Trustees of Columbia University in the City of New York, New York, N.Y.

[21] Appl. No.: 206,197

[22] Filed: Mar. 3, 1994

Related U.S. Application Data

[63] Continuation of Ser. No. 863,197, Apr. 3, 1992, abandoned.

[51] Int. Cl.$^5$ ............................................. A01N 1/02
[52] U.S. Cl. ......................................... 435/1; 435/283
[58] Field of Search ................................. 435/1, 283

[56] References Cited

U.S. PATENT DOCUMENTS

| | | | |
|---|---|---|---|
| 4,798,824 | 1/1989 | Belzer et al. | 514/60 |
| 4,927,762 | 5/1990 | Le Darfler | 435/240.31 |
| 4,963,561 | 10/1990 | Lesher et al. | 514/303 |
| 4,983,586 | 1/1991 | Bodor | 514/58 |
| 5,002,965 | 3/1991 | Ramwell et al. | 514/468 |
| 5,025,001 | 6/1991 | Loscalzo et al. | 514/91 |
| 5,145,771 | 9/1992 | Lemasters et al. | 435/1 |

OTHER PUBLICATIONS

Swanson, D. K., et al., *Transplantation*, (1979), vol. 28, No. 4, pp. 476–481, (Exhibit I).
Okouchi, Y., et al., *The Journal of Thoracic and Cardiovascular Surgery*, (1990), vol. 99, No. 6, pp. 1104–1108, (Exhibit F).
Pasque, M. K., et al., *Annals of Surgery*, (1984), vol. 200, No. 1, pp. 1–12, (Exhibit G).
Swanson, D. K., et al., *The Journal of Heart Transplantation*, (1988), vol. 7, No. 6, pp. 456–467, (Exhibit H).
Maurer, E. J., et al., *Transplantation Proceedings*, (1990), vol. 22, No. 2, pp. 548–550, (Exhibit C).
Nozaki, H., et al., *The Tohoku Journal of Experimental Medicine*, (1975), vol. 115, No. 2, pp. 145–154, (Exhibit D).
Ogawa, S., et al., *American Journal of Physiogology*, (1992), vol. 262, No. 3, pp. C546–C554, (Exhibit E).

*Primary Examiner*—Robert J. Warden
*Assistant Examiner*—Krisanne M. Thornton
*Attorney, Agent, or Firm*—John P. White

[57] ABSTRACT

The present invention provides an aqueous solution for organ preservation or maintenance, including: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about the physiologic pH value. The invention also provides a method of preserving or maintaining an organ, including contacting the organ with the solution.

43 Claims, No Drawings

SOLUTION FOR PROLONGED ORGAN PRESERVATION

This is a continuation of application Ser. No. 07/863,197, filed Apr. 3, 1992 now abandoned.

BACKGROUND OF THE INVENTION

The invention described herein was made in the course of work under Grant Number HL42507 from the Public Health Service (PHS), Department of Health and Human Services. Accordingly, the United States government has certain rights in this invention.

The present invention relates to a solution for prolonged organ preservation, and more particularly to an aqueous solution for organ preservation or maintenance. The invention also provides a method of preserving or maintaining an organ, comprising contacting the organ with the solution for organ preservation or maintenance.

Throughout this application various patents and publications are referenced and citations are provided in parentheses. The disclosure of these patents and publications in their entireties are hereby incorporated by reference into this application in order to more fully describe the state of the art to which this invention pertains.

Adequate preservation of organs intended for transplantation is critical to the proper functioning of the organ following implantation. This invention concerns an organ preservation or maintenance solution that can preserve organs intended for transplantation for periods of time that are longer than the currently best solution available. A longer preservation time is desired to enable cross-matching of donor and recipient to improve subsequent survival, as well as to allow for coast to coast and international transportation of organs to expand the donor and recipient pools. Experimental work for this invention has focused on the heart, but the organ preservation or maintenance solution of the subject invention may be used for other organs, and for tissues and cells, as well.

Many different organ preservation solutions have been designed, as investigators have sought to lengthen the time that an organ may remain extra-corporeally, as well as to maximize function of the organ following implantation. Several of the key solutions that have been used over the years include: 1) the Stanford University solution [see, e.g., Swanson, D. K., et al., Journal of Heart Transplantation, (1988), vol. 7, No. 6, pages 456–467 (mentions composition of the Stanford University solution)]; 2) a modified Collins solution [see, e.g., Maurer, E. J., et al., Transplantation Proceedings, (1990), vol. 22, No. 2, pages 548–550; Swanson, D. K., et al., supra (mention composition of modified Collins solution)]; and 3) the University of Wisconsin solution (Belzer, et al., U.S. Pat. No. 4,798,824, issued Jan. 17, 1989). Of those, the University of Wisconsin (UW) solution is currently regarded as the best. (See, e.g., Maurer, E. J., et al., supra).

In addition to the composition of the organ preservation or maintenance solution, the method of organ preservation also affects the success of preservation. Several methods of cardiac preservation have been studied in numerous publications: 1) warm arrest/cold ischemia; 2) cold arrest/macroperfusion; 3) cold arrest/microperfusion; and 4) cold arrest/cold ischemia. The first method involves arresting the heart with a warm cardioplegic solution prior to explantation and cold preservation, but this method fails because of the rapid depletion of myocardial energy store during the warm period. The second method, which involves arresting the heart with a cold preservation solution, is better; but continuous perfusion of the heart with preservation solution during the storage period fails because of the generation of toxic oxygen radicals. In addition, the procedure of the second method is cumbersome and does not lend itself to easy clinical use. The third method, first described in Nature in 1972 in a system called "trickle perfusion," is better but also cumbersome. The fourth method of preservation is that of a cold cardioplegic arrest followed by a period of cold immersion of the heart. The fourth method is currently the standard method of cardiac preservation. This fourth method reliably preserves hearts for periods of up to six (6) hours, but less than four (4) hours is considered ideal for this method. Since a longer preservation time is desirable, attempts have been made to improve preservation solutions in such a way as to reliably preserve hearts and other organs for longer periods of time.

Though the University of Wisconsin (UW) solution is currently the industry standard of organ preservation solutions, it is limited in the length of preservation time that it provides.

SUMMARY OF THE INVENTION

The organ preservation or maintenance solution of the present invention shows a substantial improvement over the prior art for increasing the preservation time for organs intended for transplantation. (See Experimental section). The organ preservation or maintenance solution of this subject invention shall also be referred to as the Columbia University (CU) solution.

The subject invention differs from other organ preservation solutions of the prior art in a number of respects.

The present invention includes a vasodilator. The vasodilator in the subject invention may be selected from the group consisting of analogues of adenosine 3',5'-cyclic monophosphate (cyclic adenosine monophosphate, cyclic-AMP, or cAMP), analogues of guanosine 3',5'-cyclic monophosphate (cyclic guanosine monophosphate, cyclic-GMP, or cGMP), nitroglycerin, adenosine, or suitable combinations thereof. Dibutyryl adenosine 3',5'-cyclic monophosphate (db cAMP) is an analogue of cAMP which is present in a preferred embodiment of the subject invention. Except for adenosine, the UW solution does not contain those vasodilators. Experimental results, to be later described, show that the subject invention improves survival of preserved rat hearts over that of the UW solution, thus demonstrating that the subject invention is more effective.

In the subject invention, the use of sodium ion, chloride ion, and calcium ion is specifically avoided. The UW solution, in contrast, contains calcium ion and chloride ion in the form of calcium chloride, and contains sodium ion in the form of sodium gluconate. (U.S. Pat. No. 4,798,824). The modified Collins solution also contains sodium ion in the form of sodium bicarbonate, and chloride ion in the form of hydrochloric acid. (Maurer, E. J., et al., supra; Swanson, et al. supra).

A preferred embodiment of subject invention also contains an agent that prevents calcium entry into cells. The UW solution, in contrast, does not contain an agent that prevents calcium entry into cells.

Both the subject invention and the UW solution contain macromolecules. However, in the subject invention dextran may be used. The patent for the UW solution, in contrast, teaches away from the use of dextran as a macromolecule. (See U.S. Pat. No. 4,798,824, col. 2, lines 15–24, which refers to the macromolecule as a colloid).

Another difference is that a preferred embodiment of the subject invention contains N-acetylcysteine, whereas the UW solution does not contain N-acetylcysteine. The present invention does not contain glutathione, while the UW solution does. During organ preservation, glutathione is lost from the organ. However, it is now known that glutathione in solution does not enter easily into the cell. N-acetylcysteine, however, can enter cells more easily, and is believed to be an agent that helps cells produce glutathione.

Another difference between the subject invention and the modified Collins organ preservation solutions is the choice of buffer. Because basal metabolism results in the generation of acid (the pH of the organ preservation solution can decline during storage), a phosphate buffering system (monopotassium phosphate ($KH_2PO_4$)) is used in a preferred embodiment of the subject invention. The subject invention specifically avoids the use of a bicarbonate buffer. The subject invention has the advantage over other organ preservation solutions that use a bicarbonate buffering system, because a bicarbonate buffering system poses the problem of carbon dioxide removal during buffering. A bicarbonate buffer is used in the modified Collins solution (Maurer, E. J., et al. supra; Swanson, et al. supra).

The initial pH of a preferred embodiment of the subject invention is to the alkaline side of normal physiologic pH so that the average pH during storage remains physiologic. Normal physiologic pH is about 7.4. In other organ preservation solutions that start at or near a physiologic pH, an organ would spend the bulk of a prolonged storage period in a state of acidosis. For instance, the University of Wisconsin solution claims a pH range of 7.4–7.5. In contrast, a preferred embodiment of the subject invention has an initial pH range of about 7.4 to about 7.6.

An investigation of the literature reveals no teaching or suggestion for the use of analogues of adenosine 3',5'-cyclic monophosphate (cyclic adenosine monophosphate, cyclic-AMP, or cAMP), or analogues of guanosine 3',5'-cyclic monophosphate (cyclic guanosine monophosphate, cyclic-GMP, or cGMP), in an organ preservation solution, although there have been studies investigating the effectiveness of various organ preservation solutions. (See, e.g., Okouchi, Yasumitsu, et al., Journal of Thoracic and Cardiovascular Surgery, (1990), vol. 99, pages 1104–1108; Maurer, E. J., et al., supra; Swanson, et al. supra). There has also been significant research into the biochemical mechanisms involved in the metabolic changes associated with myocardial ischemia and reperfusion. (See, e.g., Pasque, Michael K., and Wechsler, Andrew S., Annals of Surgery, (1984), vol. 200, pages 1–12; Nozaki, Hirofumi, and Okuaki, Akira, Tohoku Journal of Experimental Medicine, (1975), vol. 115, pages 145–154; Ogawa, S. et al., American Journal of Physiology, (1992), vol. 262, pages C546–C554).

Such research has shown that endothelial cell monolayers lose their integrity when exposed to hypoxia, which simulates a significant component of ischemia. Following a twelve hour exposure of an aortic endothelial cell monolayer to hypoxia, the monolayer is disrupted, and large gaps form between cells. The "leakiness" of the monolayer can be evaluated by the transfer of various sized radioactive compounds across it, and it is clear that this "leakiness" increases as duration of hypoxic exposure increases. (See, e.g., Ogawa, S. et al., supra). Thus the barrier function of the monolayer is lost.

This loss of endothelial cell barrier function parallels a decline in intracellular adenosine 3',5'-cyclic monophosphate (cyclic adenosine monophosphate, cyclic-AMP, or cAMP) levels. (See, e.g., Pasque, Michael K., and Wechsler, Andrew S., supra; Ogawa, S. et al., supra). Experiments have shown that this hypoxia-induced increase in endothelial cell permeability could be abrogated by maneuvers designed to increase intracellular cyclic-AMP concentration, such as the addition of pertussis toxin. (See, e.g., Ogawa, S. et al., supra). Experiments have also shown that the addition of cyclic-AMP analogues could restore the integrity of the endothelial cell monolayer to solutes of various sizes. (See, e.g., Nozaki, Hirofumi, and Okuaki, Akira, supra; Ogawa, S. et al., supra). Apparently, cyclic-AMP can not penetrate the cell membrane as easily as analogues of cyclic AMP. Dibutyryl adenosine 3',5'-cyclic monophosphate (db cAMP), is an analogue of cyclic-AMP. (See, e.g., Nozaki, Hirofumi, and Okuaki, Akira, supra).

None of that research has disclosed or suggested the use of analogues of cAMP or of cGMP for use in an organ preservation or maintenance solution. Analogues of cAMP or of cGMP that are permeable to the cell membrane can be used in the subject invention.

Analogues of cAMP are believed both to serve as a vasodilator, and to help maintain endothelial integrity. Analogues of cGMP, however, are believed to function as a vasodilator, while their role in helping to maintain endothelial integrity is presently less certain. Hence, the subject invention may use analogues of cGMP as vasodilators. But a preferred embodiment of the subject invention includes analogues of cAMP, because analogues of cAMP are believed to serve both as a vasodilator and to help maintain endothelial cell integrity. Hence, a preferred embodiment of the invention contains db cAMP, which is an analogue of cAMP. It is believed that analogues of cAMP may enhance endothelial barrier function during cold ischemia, which is a step during organ preservation, thereby improving organ function following preservation. Other chemical or physiological mechanisms may be involved.

The present invention provides an aqueous solution for organ preservation or maintenance, comprising: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about the physiologic pH value.

The invention also provides a method of preserving or maintaining an organ, comprising contacting the organ with the solution for organ preservation or maintenance.

DETAILED DESCRIPTION OF THE INVENTION

The present invention provides an aqueous solution for organ preservation or maintenance, comprising: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about the physiologic pH value.

This invention concerns an organ preservation or maintenance solution that can preserve an organ wherein the organ is an organ intended for transplantation. For example, the organ intended for transplantation may be a heart. While experimental work for this invention has focused on the heart, the organ preservation or maintenance solution may be used for other organs, and for tissues and cells as well, because the same principles of organ preservation apply.

The organ preservation or maintenance solution can also be used for maintaining organs during surgery, because the principles of organ preservation apply. For example, the organ preservation or maintenance solution may be used during cardiac, or open heart, surgery, as a cardioplegic solution. Other uses of the subject invention may be obvious to those skilled in the medical profession.

In general, the principles of organ preservation recognize that organ viability must be maintained at two different levels during and after preservation: at the tissue level, and at the cellular level.

At the tissue level, vascular integrity must be maintained so that tissue architecture, nutrient delivery, and toxin removal are nearly normal. As described below, a preferred embodiment of the organ preservation solution contains analogues of adenosine 3',5'-cyclic monophosphate (cyclic adenosine monophosphate, cyclic-AMP, or cAMP), such as db cAMP, which help maintain endothelial integrity in conditions of hypoxia, such as during preservation, and are also believed to be important for the reperfusion period. It is believed that analogues of cAMP may enhance endothelial barrier function during cold ischemia, which is a step during organ preservation, thereby improving organ function following preservation. The analogues of adenosine 3',5'-cyclic monophosphate probably also function as vasodilators Dibutyryl adenosine 3',5'-cyclic monophosphate (db cAMP), which is an analogue of adenosine 3',5'-cyclic monophosphate, is present in a preferred embodiment. Analogues of cAMP are believed both to serve as a vasodilator, and to help maintain endothelial cell integrity.

Analogues of cGMP, however, are believed to function as a vasodilator, while their role in helping to maintain endothelial cell integrity is presently less certain. Hence, the subject invention may use analogues of cGMP as vasodilators. But a preferred embodiment includes analogues of cAMP, because analogues of cAMP serve both as a vasodilator and to help maintain endothelial cell integrity. Other chemical or physiological mechanisms may be involved.

Other components also help maintain vascular integrity. Macromolecules of molecular weight greater than 20,000 daltons help plug small endothelial leaks which may occur, preventing extravasation of intravascular contents into the pericellular space. An anticoagulant, which is present in a preferred embodiment, helps prevent thrombosis during or after preservation, so that nutrient delivery and toxin removal can proceed. Vasodilators, such as analogues of adenosine 3',5'-cyclic monophosphate, analogues of guanosine 3',5'-cyclic monophosphate, nitroglycerin, or adenosine are probably also important for similar reasons, so that vascular homeostasis can be re-achieved rapidly following reimplantation.

The principles of organ preservation also suggest that maintenance of cellular viability is likewise important to proper organ function following transplantation. In that regard, the organ preservation or maintenance solution contains a macromolecule of molecular weight greater than 20,000 daltons, which helps prevent cellular swelling and rupture during the preservation and recovery periods. The macromolecule of molecular weight greater than 20,000 daltons includes colloids. Also, the osmolarity of the organ preservation must be greater than the cellular osmolarity. The organ preservation or maintenance solution also contains D-glucose and magnesium ions, because basal energy metabolism (even during hypothermia) can be supported by the anaerobic metabolism of glucose, and the presence of magnesium ions allows for the proper functioning of the enzymes needed for adenosine triphosphate (ATP) synthesis. Adenosine is also present in a preferred embodiment, since adenosine may be a substrate for ATP synthesis. A preferred embodiment also contains antioxidants or reducing agents, since following reperfusion, highly toxic oxygen radicals are known to be formed, and the addition of such agents help serve to mute the lethal effects of these radicals during the vulnerable period immediately following re-establishment of blood flow. A preferred embodiment also contains an agent that helps prevent calcium entry into cells, because it is also well known that calcium accumulation within a cardiac myocyte can be injurious or lethal following reperfusion. Hence, the organ preservation or maintenance solution does not contain calcium, and a preferred embodiment contains an agent that helps prevent calcium entry into cells.

The organ preservation or maintenance solution comprises a vasodilator in an amount sufficient to maintain vascular homeostasis. The vasodilator can be selected from the group consisting of analogues of adenosine 3',5'-cyclic monophosphate (cyclic adenosine monophosphate, cyclic-AMP, or cAMP), analogues of guanosine 3',5'-cyclic monophosphate (cyclic guanosine monophosphate, cyclic-GMP, or cGMP), nitroglycerin, or adenosine. Suitable combinations of the vasodilators may be used. A preferred embodiment contains a vasodilator, wherein the vasodilator is dibutyryl adenosine 3',5'-cyclic monophosphate (db cAMP), alone or in combination with nitroglycerin and adenosine.

Recent experiments have shown that some vasodilators are more effective than others. In particular, recent experiments have shown that analogues of adenosine 3',5'-cyclic monophosphate and nitroglycerin are important; but that the organ preservation or maintenance solution will function without the presence of adenosine. A preferred embodiment, however, contains adenosine. (See Experimental section).

Further recent experiments suggest that the organ preservation and maintenance solution may function without the presence of db cAMP, so long as the solution contains nitroglycerin. (See Experimental section). It is believed, however, that the solution functions more effectively with the presence of db cAMP in addition to the nitroglycerin. Though it is difficult to assess the relative importance of the individual components of the organ preservation and maintenance solution, the presence of vasodilators is clearly important.

The analogues of adenosine 3',5'-cyclic monophosphate can be selected from the group consisting of dibutyryl adenosine 3',5'-cyclic monophosphate (db cAMP), or 8-bromoadenosine 3',5'-cyclic monophosphate. As mentioned earlier, other suitable analogues of cAMP may be used.

Experiments have shown that adenosine 3',5'-cyclic monophosphate (cyclic-AMP, or cAMP) has difficulty entering the cell membrane, but that analogues of cAMP are more permeable. Experiments also have shown that it is the cAMP portion of the molecule that exerts a beneficial effect. (See Experimental section). Hence, other analogues of cAMP or of cGMP which can enter the cell membrane can be used.

Vasodilators are important for ensuring that thrombosis does not occur during or after preservation, so that nutrient delivery and toxin removal can proceed. Vasodilators thus help vascular homeostasis to be re-achieved rapidly following re-implantation. Recent evidence indicates that adenosine may act via the adenosine receptor (causing vasodilation) to minimize damage following experimental canine myocardial infarction and reperfusion. In fact, the major salutary role of db cAMP in organ preservation or maintenance may be via its actions as a vasodilator. Vasodilators are likely to be necessary if vasospasm plays any role in the post-implantation period, as it likely does.

Analogues of cAMP are believed to make hearts, and other organs, less susceptible to reperfusion injury. The addition of such analogues of cAMP help serve to maintain endothelial integrity in conditions of hypoxia (such as during preservation), as well as during reperfusion.

Db cAMP is an example of an analogue of cAMP which can be used in the organ preservation or maintenance solution. The optimal concentration of db cAMP is about 2 mM, though the solution functions with db cAMP concentrations of about 1 mM, and of about 2 to 4 mM. (See Experimental section). Experiments have shown, however, that db cAMP concentrations higher than about 4 mM become toxic to endothelial cells. Hence, 2 mM is considered to be the optimal concentration of db cAMP. In a preferred embodiment, the concentration of dibutyryl adenosine 3',5'-cyclic monophosphate (db cAMP) ranges from about 1 mM to about 4 mM.

The organ preservation or maintenance solution may also comprise nitroglycerin. In a preferred embodiment, the concentration of nitroglycerin ranges from about 0.05 g/l to about 0.2 g/l.

The organ preservation or maintenance solution may also comprise adenosine. In a preferred embodiment, the concentration of adenosine ranges from about 3 mM to about 20 mM.

The organ preservation or maintenance solution also comprises D-glucose in an amount sufficient to support intracellular function and maintenance of cellular bioenergetics. In a preferred embodiment, the concentration of D-glucose ranges from about 50 mM to about 80 mM.

The organ preservation or maintenance solution also comprises magnesium ions in an amount sufficient to support intracellular function and maintenance of cellular bioenergetics. In a preferred embodiment, the concentration of magnesium ions ranges from about 2 mM to about 10 mM. The magnesium ions are derived from the group consisting of magnesium sulfate, magnesium gluconate, or magnesium phosphate, or suitable combinations thereof. The magnesium ions can be derived from some other suitable magnesium containing compound.

D-Glucose, adenosine, and magnesium ions are substrates for adenosine triphosphate (ATP) synthesis. Metabolic substrates such as D-glucose and perhaps adenosine for ATP formation are probably important for maintaining the small degree of anaerobic metabolism that occurs. Basal energy metabolism (even during hypothermia) can be supported by the anaerobic metabolism of D-glucose. The presence of magnesium ion allows for the proper functioning of the enzymes needed for adenosine triphosphate (ATP) synthesis. In general, substrates for ATP synthesis are helpful to allow intracellular function and maintenance of cellular bioenergetics.

The organ preservation or maintenance solution also comprises macromolecules of molecular weight greater than 20,000 daltons in an amount sufficient to maintain endothelial integrity and cellular viability. In a preferred embodiment, the macromolecule of molecular weight greater than 20,000 daltons is selected from the group consisting of macromolecules having a molecular weight greater than about 100,000 daltons, a polysaccharide, or a polyethylene glycol. Other suitable macromolecules can be used. The macromolecule of molecular weight greater than 20,000 daltons can include colloids.

In a preferred embodiment, the polysaccharide is a dextran. Furthermore, in a preferred combination, the dextran is a dextran molecule having a molecular weight of 308,000 daltons.

It is difficult to define an upper limit to the molecular weight of the macromolecule of molecular weight greater than 20,000 daltons. For instance, the macromolecule can be dextran, having a molecular weight of 308,000 daltons.

Macromolecules of molecular weight greater than 20,000 daltons are believed to be helpful in reducing trans-endothelial leakage and subsequent intracellular and interstitial edema in the reperfusion period, by serving to plug small endothelial leaks which may occur. Macromolecules may thus also prevent the extravasation of intravascular contents into the pericellular space, thus helping to prevent cellular swelling and rupture during the preservation and recovery periods.

The osmolarity of the organ preservation or maintenance solution is also a factor in helping to prevent cellular swelling and rupture. The osmolarity of the organ preservation or maintenance solution must be greater than the cellular osmolarity. Cellular osmolarity is about 290 mOsm/l. In a preferred embodiment, the osmolarity ranges from about 315 mOsm/l to about 340 mOsm/l.

The organ preservation or maintenance solution also comprises potassium ions in a concentration greater than about 110 mM. The potassium ions are derived from the group consisting of potassium sulfate, potassium gluconate, monopotassium phosphate (KH$_2$PO$_4$), or suitable combinations thereof. The potassium ions may be derived from some other suitable potassium containing compound. In a preferred embodiment, the concentration of potassium ions ranges from about 110 mM to about 140 mM.

The design of the solution encompasses the need for a high potassium concentration, similar to intracellular levels, as this aids both in the cardioplegic aspects of the solution and has been shown to enhance myocardial viability following cold potassium cardioplegia.

The organ preservation or maintenance solution also comprises a buffer in an amount sufficient to maintain the average pH of the organ preservation or maintenance solution during the period of organ preservation at about the physiologic pH value. In a preferred embodiment, the buffer is monopotassium phosphate (KH$_2$PO$_4$). However, other suitable buffers may be used.

The buffering capacity must be adequate to buffer the organic acids that accrue during ischemia. Because basal metabolism results in the generation of acid, a buffering system is used. The pH of the organ preservation or maintenance solution declines during the prolonged storage times that can be employed with this solution. A bicarbonate buffering system, however, is not used in the subject invention because a bicarbonate buffer would release carbon dioxide, which would have to be removed.

In a preferred embodiment, the initial pH of the organ preservation or maintenance solution is adjusted to the alkaline side of normal physiologic pH because then the average pH during storage of the organ in the organ preservation or maintenance solution remains physiologic. Normal physiologic pH is about 7.4. A preferred embodiment of the organ preservation or maintenance solution has a pH range of about 7.4 to about 7.6. The pH may be adjusted to the desired value with the addition of a suitable base, such as potassium hydroxide (KOH). Hence, during the period of organ preservation, the pH of the organ preservation or maintenance solution starts on the alkaline side of physiologic pH, and may drift slowly down to the acidic side of physiologic pH. But the average pH of the organ preservation or maintenance solution during the period of organ preservation is about the physiologic value.

The organ preservation or maintenance solution may further comprise impermeant anions in an amount sufficient to help maintain endothelial integrity and cellular viability. The impermeant anion is selected from the group consisting of the gluconate anion or the lactobionate anion. Other suitable impermeant anions can be used. In a preferred embodiment, the concentration of the gluconate anion ranges from about 85 mM to about 105 mM. The gluconate anion is derived from the group consisting of potassium gluconate or magnesium gluconate. The gluconate anion may be derived from some other suitable gluconate containing compound.

Impermeant anions are large anions that cannot cross cell membranes, so that sodium is at least in part prevented from diffusing down its concentration gradient into the cell during the preservation period. Impermeant anions thus help to prevent cellular edema.

The organ preservation or maintenance solution may further comprise an anticoagulant in an amount sufficient to help prevent clotting of blood within the capillary bed of the organ. The anticoagulant is selected from the group consisting of heparin or hirudin. Other suitable anticoagulants may be used. In a preferred embodiment, the concentration of heparin ranges from about 1000 units/l to about 100,000 units/l.

Anticoagulants are believed to help in preventing clotting of blood within the capillary bed of the preserved organ. Specifically, anticoagulants are believed to help prevent a total organ no-reflow phenomenon at the level of the microcirculation, which would be undesirable following re-implantation and could result in graft failure. Anticoagulants are believed to be helpful in ensuring that thrombosis does not occur during or after preservation, so that nutrient delivery and toxin removal can proceed.

The organ preservation or maintenance solution may further comprise an antioxidant in an amount sufficient to help decrease reperfusion injury secondary to oxygen free radicals. The antioxidant is selected from the group consisting of butylated hydroxyanisole (BHA), butylated hydroxytoluene (BHT), Vitamin C, Vitamin E, or suitable combinations thereof. Other suitable antioxidants may be used. In a preferred embodiment, the antioxidant is butylated hydroxyanisole (BHA) at a concentration range from about 25 microM to about 100 microM, alone or in combination with butylated hydroxytoluene (BHT) at a concentration range from about 25 microM to about 100 microM.

The organ preservation or maintenance solution may further comprise a reducing agent in an amount sufficient to help decrease reperfusion injury secondary to oxygen free radicals. Any suitable reducing agent can be used.

The organ preservation or maintenance solution may further comprise N-acetylcysteine in an amount sufficient to help cells produce glutathione. In a preferred embodiment, the concentration of N-acetylcysteine ranges from about 0.1 mM to about 5 mM.

N-acetylcysteine is an agent which can enter cell and is believed to play a role in helping cells to produce glutathione, which is a reducing agent. During organ preservation, glutathione is lost from the organ. Simply adding glutathione to the organ preservation or maintenance solution, however, would be of little to no help, because it is now known that glutathione in solution does not enter easily into the cell.

The organ preservation or maintenance solution may further comprise an agent that helps prevent calcium entry into cells in an amount sufficient to help prevent calcium entry into cells. Agents that help prevent calcium entry into cells include so-called calcium channel blockers, as well as other agents that serve the described function. An agent that helps prevent calcium entry into cells is verapamil. Other suitable agents that help prevent calcium entry into cells may be used. In a preferred embodiment, the concentration of verapamil ranges from about 2 microM to about 25 microM.

Agents that help prevent calcium entry into cells are believed to play a role in preventing calcium overload as a cause for myocyte death during and after preservation. It is also well known that calcium accumulation within a cardiac myocyte can be injurious or lethal following reperfusion. Hence, the organ preservation or maintenance solution specifically does not contain calcium.

The absence of sodium in the organ preservation or maintenance solution is also by design, because any sodium which may enter the cells during the period of preservation (when energy currency is low and the normal trans-cellular gradient may not be well maintained) may 1) lead to cellular swelling, 2) cause calcium entry by facilitated diffusion (following re-implantation), and 3) sodium load the cell and hence depolarize it during storage, such that a high amount of energy is required following reestablishment of blood flow before a normal membrane potential can be re-established. In fact, sodium loading is well described during hypothermic storage of organs.

Electrolyte concentrations must be adjusted to reduce transmembrane flux of electrolytes. The absence of chloride in the organ preservation or maintenance solution is also by design. Sodium, chloride, and calcium are avoided.

The organ preservation or maintenance solution may further comprise a bacteriostat in an amount sufficient to help inhibit the growth of, or destroy, bacteria. The bacteriostat is selected from the group consisting of cefazolin or penicillin. Other suitable bacteriostats or antibiotics can be used. In an embodiment, the concentration of cefazolin ranges from about 0.25 g/l to about 1 g/l.

The addition of an antibiotic to the organ preservation or maintenance solution is purely a surgical consideration, due to the practical inability of sterilizing the solution completely, as the high molecular weight solutes would not pass through a 0.2 micron membrane filter which is used in the preparation of the organ preservation or maintenance solution. It is believed that gamma irradiation may be used to better sterilize the solution. The possible use of gamma irradiation for sterilization will require experimental investigation.

The invention also provides a method of preserving or maintaining an organ, comprising contacting the organ with the solution for organ preservation or maintenance. The contacting comprises immersion, infusion, flushing, or perfusion. Other suitable procedures of contacting are included. The method can be used wherein the organ is an organ intended for transplantation. The method can be used wherein the organ is a heart. For example, the method can be used wherein the heart is involved in cardiac surgery. Hence, the organ preservation or maintenance solution may be used in organ transplantation procedures. The organ preservation or maintenance solution may also be used during certain other surgical or medical procedures; for example, the solution may be used as a cardioplegic agent during cardiac surgery.

Experiments involving the organ preservation or maintenance solution have involved the heart. However, it is anticipated that similar principles of organ preservation apply to other organs as well, such that the organ preservation or maintenance solution might be used successfully to preserve livers, pancreases, kidneys, lungs, etc. For instance, a preliminary and recent experiment has been performed involving the transplantation of a single baboon lung wherein the lung was preserved in the solution for twenty-two hours. (See Experimental section). In general, the organ preservation or maintenance solution may be used for cells and tissues, as well as for organs. That is, the organ preservation or maintenance solution may be used for those situations that require cell viability.

In addition, the principles of organ preservation apply to cardioplegic agents used to arrest the heart during cardiac surgery, so that the organ preservation or maintenance solution may have a role as a cardioplegic agent independent of transplant surgery. The solution may also be used for other medical procedures.

Because myocardial infarction also involves ischemic (and often reperfusion) phases, there is a potential role for the organ preservation or maintenance solution for myocardial salvage following infarction, thrombolysis, or complicated angioplasty. The organ preservation or maintenance solution thus provides a clear advantage over other organ preservation solutions designed to date, and the principles involved in its design likely apply to a host of important clinical situations.

The composition of the organ preservation or maintenance solution might have to be adjusted according to the type of organ being transplanted, or to accommodate certain other surgical, medical, or other considerations. The composition of the organ preservation or maintenance solution might also be different when the solution is being used as a cardioplegic agent in cardiac surgery, or in some other appropriate surgical procedure, than when the solution is being used for organ transplantation. The composition might also require adjustment depending upon certain other circumstances. For instance, the composition might have to be varied depending upon whether the organ is being transported or is in idle storage, the distance of the transportation, the time of transportation, the temperature during storage or transportation, and other factors. Such variations or adjustments in the composition of the organ preservation or maintenance solution which might be required would be obvious to those skilled in organ transplantation or surgical procedures.

The amount of the organ preservation or maintenance solution required in an organ transplantation or surgical procedure (such as a cardioplegic agent during cardiac surgery) would be obvious to one who is skilled in such organ transplantation or surgical procedures.

The organ preservation or maintenance solution is suitable for use at the low temperatures that may be required during an organ transplantation or other surgical procedure. For instance, temperatures of about zero to about four degrees Centigrade may be required during an organ transplantation or surgical procedure.

The best embodiment of the subject invention consists of the following ingredients in the amounts specified:

D-Glucose, 67.4 mM
Magnesium Sulfate ($MgSO_4$), 5 mM
Monopotassium Phosphate ($KH_2PO_4$), 25 mM
Dextran (molecular weight 308,000 daltons), 50 g/l
Potassium Gluconate (K-Gluconate), 95 mM
Butylated Hydroxyanisole (BHA), 50 microM
Butylated Hydroxytoluene (BHT), 50 microM
N-Acetylcysteine (N-AC), 0.5 mM
Adenosine, 5 mM
Nitroglycerin, 0.1 g/l
Verapamil, 10 microM
Dibutyryl Adenosine 3',5'-Cyclic Monophosphate (Dibutyryl cAMP, db cAMP), 2 mM
Heparin, 10,000 units/l
Cefazolin, 0.5 g/l The pH is adjusted to 7.6 with Potassium Hydroxide (KOH). The organ preservation or maintenance solution is an aqueous solution.

A method of preparing the organ preservation or maintenance solution is described in the Experimental Details section.

Certain embodiments of the invention are set forth in the Experimental Details section which follows. The Experimental Details section is provided to aid in an understanding of the invention but is not intended to, and should not be construed to, limit in any way the invention as set forth in the claims which follow thereafter.

EXPERIMENTAL DETAILS

Experiment One

In Experiment One, a heterotopic rat heart transplant model is used [Okouchi, Yasumitsu, et al., Journal of Thoracic and Cardiovascular Surgery, vol. 99 (1990), pages 1104–1108 (heterotopic rat heart transplant model)] to examine the comparative effectiveness of the organ preservation or maintenance solution of the subject invention.

MATERIALS AND METHODS

The following reagents were obtained from the indicated commercial sources; D-glucose, magnesium sulfate, dextran (M.W. 308,000 daltons), monopotassium phosphate ($KH_2PO_4$), potassium gluconate, adenosine, butylated hydroxyanisole (BHA), butylated hydroxytoluene (BHT), N-acetylcysteine (N-AC), and heparin (porcine intestinal, 100000 u/g) were obtained from Sigma Chemical Company (St. Louis, Mo.). Dibutyryl adenosine 3',5'-cyclic monophosphate (dibutyryl cyclic AMP, or db cAMP) was obtained from Aldrich Chemical Company, Incorporated (Milwaukee, Wis.). Verapamil (2.5 mg/ml) was obtained from Knoll Pharmaceutical Co. Nitroglycerin (5 mg/ml) was obtained from DuPont (Manati, Puerto Rico). Cefazolin (400 mg/ml) was obtained from Lyphomed (Rosemont, Ill.). Lactated Ringer's solution was obtained from Abbott (North Chicago, Ill.).

Columbia University solution is made by adding 67.4 mM D-glucose, 5 mM magnesium sulfate ($MgSO_4$), 95 mM potassium gluconate, 25 mM monopotassium phosphate ($KH_2PO_4$), and 10 units/ml of heparin to double distilled water. The pH is then adjusted to about 7.6 with 10M potassium hydroxide (KOH). The solution is then filtered with a 0.2 micron filter. Dextran (50 g/l) (molecular weight 308,000 daltons) is added with gentle stirring for 24 hours at 4° C. to aid dissolution and to help de-bubble the mixture. On the morning of use, cefazolin (0.5 mg/ml), adenosine (5 mM), nitroglycerin (0.1 mg/ml), Verapamil (10 microM), BHA (50 μM), BHT (50 μM), N-acetylcysteine (0.5 mM), and db cAMP (2 mM) are added (the BHA and BHT were first dissolved in ethanol at 50 mM to aid solubility).

A heterotopic rat heart transplant model is used to examine the comparative effectiveness of the organ preservation or maintenance solution of the subject invention. The heterotopic rat heart transplant model involves harvesting a heart following cold cardioplegic arrest, and then flushing the aortic root with preservation solution until the coronary arteries become visibly clear. Following a period of preservation, the heart is then transplanted into a recipient rat's abdomen with the aortic root being anastomosed to the recipient's abdominal aorta, and the pulmonary artery being anastomosed to the recipient's inferior vena cava. This permits normal coronary artery perfusion of the transplanted heart following implantation.

Male Sprague-Dawley rats (350–400 gm) were prepared as follows. Each donor rat was anesthetized, shaved, given 1000 units of heparin intravenously (IV), and explanation was begun one (1) minute later. A midline longitudinal incision was made spanning the thorax and abdomen, the suprahepatic inferior vena cava was ligated, and 5 cc of cold cardioplegia (Ringers Lactate (RL) with 40 milliequivalent KCl/l) was administered into the inferior vena cava (IVC). Although Ringer's Lactate solution was used for that purpose in these experiments, the organ preservation or maintenance solution of the subject invention may also be used. A cold saline-soaked gauze was kept over the heart for the following manipulations. The superior vena cava (SVC) was ligated and transected, after which a suture was passed underneath the aortic arch and mainstem pulmonary artery, and looped back under the suprahepatic IVC. The aorta and mainstem pulmonary artery were then transected approximately 4 mm from their respective origins. The suture that had been placed was gathered in a purse-string fashion to encompass all pulmonary veins, which were then ligated. The heart was removed by transecting the IVC and the pulmonary veins, and then rapidly immersed in 4° C. preservation solution. For the purposes of this portion of the experiment, the "preservation solution" here is one of five test solutions: 1) Ringer's Lactate (RL); 2) Ringer's Lactate to which 4 mM of db cAMP is added; 3) University of Wisconsin (UW) solution; 4) University of Wisconsin solution to which 4 mM of db cAMP is added; or 5) the subject invention (Columbia University solution). The aortic root was flushed with preservation solution until the coronaries were clear (approximately 15 ml per heart), and the IVC was again ligated closer to its insertion into the right atrium, and excess tissue trimmed away. The explanted heart was kept immersed in the preservation solution (kept on crushed ice) for the indicated duration of time.

The recipient rat was anesthetized in a similar fashion as the donor, but was not heparinized. A longitudinal midline abdominal incision was performed, and the abdominal aorta and IVC were gathered in a cross-clamp. 8-0 nylon material was used to suture the donor aorta to the recipient aorta, after which the donor pulmonary artery was anastomosed to the recipient IVC in a similar fashion. The donor heart was kept moist with a cold saline-soaked gauze throughout this period of reanastomosis. The duration of preservation was considered to be that from the time of harvest to the time of release of the aortic cross-clamp. The period of warm ischemia, that is, the time from initiation of implantation until release of cross claim was always kept at one (1) hour.

Following release of the aortic cross-clamp, the transplanted hearts are scored from zero to five (worst to best) based on the criteria of turgor [hard (0), average (1), and soft (2)]; color [not-pink (0) and pink (1)]; and contraction [poor (0), average (1), and good (2)]. The worst appearance is when the transplanted hear is not beating, hard, and black. In fact, often the failed transplant can be seen to go from pale immediately out of cold preservation, to pink as the blood perfuses the heart, to black, as the graft becomes non-viable, and this occurs over a period of a few minutes. For this reason, hearts were scored at ten minutes following release of the aortic cross-clamp, to obtain the "Heart Transplant Index." Electrocardiograms (EKG) were also taken at this time to obtain the "Heart Survival Rate." A regular EKG rhythm was necessary for the overall transplant to have been considered a success.

Also examined was a comparison of db cAMP (4 mM) with other agents for cardiac preservation, where those other agents consisted of Na Butyrate (4 mM); 8-Bromoadenosine 3',5'-cyclic monophosphate (4 mM); and 8-Bromoadenosine (4 raM).

Also examined was the effect of the concentration of db cAMP on both Ringer's Lactate and University of Wisconsin solutions.

Finally, Ringer's Lactate solution, University of Wisconsin solution, and University of Wisconsin solution to which db cAMP was added, were compared to the organ preservation or maintenance solution of the subject invention (Columbia University solution) at a preservation time of twenty-eight (28) hours.

DATA

TABLE I

Comparison of Five Preservation Solutions

Table I A:
Effect of db cAMP on Cardiac Preservation in Ringer's Lactate Solution

| Time | RL (A) | RL + dbcAMP (A) | RL (B) | RL + dbcAMP (B) |
|---|---|---|---|---|
| 4 hr | 3/3 | 6/6 | 5 | 5 |
| 8 hr | 1/6 | 3/3 | aprx. 1.5 | 5 |
| 12 hr | 0/9 | 9/9* | 0.8 ± 0.4 | 4.6 ± 1.3* |

TABLE I B:
Effect of db cAMP on Cardiac Preservation in University of Wisconsin Solution

| Time | UW (A) | UW + dbcAMP (A) | UW (B) | UW + dbcAMP (B) |
|---|---|---|---|---|
| 16 hr | 4/6 | 5/5 | aprx. 3.5 | aprx. 4.8 |
| 20 hr | 1/3 | 5/5 | aprx. 2.0 | aprx. 4.7 |
| 24 hr | 3/9* | 9/9 | 1.9 ± 1.4* | 4.7 ± 0.7 |
| 28 hr | 4/9 | 6/10 | 2.4 ± 1.6 | 3.2 ± 1.8 |

TABLE I C:
Effect of Columbia University Solution on Cardiac Preservation

| Time | CU (A) | CU (B) |
|---|---|---|
| 24 hr | 6/6 | 4.8 ± 0.4 |
| 28 hr | 12/13* | 4.6 ± 0.9 |
| 36 hr | 33.3% | aprx. 4.6 |

TABLE I D:
Comparison of Ringer's Lactate Solution, University of Wisconsin Solution, and University of Wisconsin Solution to Which db cAMP is Added, With Columbia University Solution (Subject Invention), at Preservation Times of 28 and 36 Hours

| Time | RL (A) | UW (A) | UW + dbcAMP (A) | CU (A) |
|---|---|---|---|---|
| 28 hr | zero | 4/9 | 6/10 | 12/13 |
| 36 hr | — | — | — | 33.3% |

| Time | RL (B) | UW (B) | UW + dbcAMP (B) | CU (B) |
|---|---|---|---|---|
| 28 hr | zero | 2.3 ± 1.2 | 3.2 ± 1.2 | 4.6 ± 1 |
| 36 hr | — | — | — | aprx. 4.6 |

In Table I above, the symbols and abbreviations have the following meanings:

A is heart survival rate, or function (rhythm on EKG), (#viable/#attempted); B is transplant index, or appearance, based on turgor, color, and contractility, ranging from zero to five (worst to best); hr is time in hours; aprx. is approximately; CU is Columbia University solution (the subject invention); RL is Ringer's Lactate solution; RL+db cAMP is Ringer's Lactate solution to which 4 mM of db cAMP is added; UW is University of Wisconsin solution; UW+db cAMP is University of Wisconsin solution to which 4 mM of db cAMP is added; (*) denotes p is less than 0.05 from other values at same time value (—) denotes that there is no experimental data.

TABLE II

Comparison of db cAMP With Other Agents For Cardiac Preservation, at Preservation Time of 24 Hours

| Time | CU (A) | XX (A) | YY (A) | ZZ (A) |
|---|---|---|---|---|
| 24 hr | 9/9 | 0/3 | 6/7 | 1/6 |

| Time | CU (B) | XX (B) | YY (B) | ZZ (B) |
|---|---|---|---|---|
| 24 hr | aprx. 5 | aprx. 1 | aprx. 4.6 | aprx. 2 |

In Table II, the symbols have the following meanings:

A is heart survival rate, or function (rhythm on EKG), (#viable/#attempted); B is transplant index, or appearance, based on turgor, color, and contractility, ranging from 0–5 (worst to best); hr is time in hours; aprx. is approximately; CU is Columbia University solution with a db cAMP concentration value of 4 mM; XX is a solution containing components of the Columbia University solution, but replacing the db cAMP with Na Butyrate (4 mM); YY is a solution containing components of the Columbia University solution, but replacing the db cAMP with 8-Bromoadenosine 3',5'cyclic monophosphate (4 mM); ZZ is a solution containing components of the Columbia University solution, but replacing the db cAMP with 8-Bromoadenosine (4 mM).

TABLE III

Effect of Concentration of db cAMP in Ringer's Lactate Solution and University of Wisconsin Solution

| Time | RL (A) | RL + 0.1 mM db cAMP (A) | RL + 1.0 mM db cAMP (A) | RL + 4.0 mM db cAMP (A) |
|---|---|---|---|---|
| 12 hr | 0/9 | 0/3 | 3/3 | 9/9 |

| Time | RL (B) | RL + 0.1 mM db cAMP (B) | RL + 1.0 mM db cAMP (B) | RL + 4.0 mM db cAMP (B) |
|---|---|---|---|---|
| 12 hr | aprx. 0.8 | aprx. 0.7 | 5 | 5 |

| Time | UW (A) | UW + 0.1 mM db cAMP (A) | UW + 1.0 mM db cAMP (A) | UW + 4.0 mM db cAMP (A) |
|---|---|---|---|---|
| 12 hr | aprx. 33% | aprx. 33% | 100% | 100% |

| Time | UW (B) | UW + 0.1 mM db cAMP (B) | UW + 1.0 mM db cAMP (B) | UW + 4.0 mM db cAMP (B) |
|---|---|---|---|---|
| 12 hr | aprx. 1.8 | aprx. 3.4 | aprx. 5 | aprx. 4.7 |

In Table III, the symbols have the following meanings:

A is heart survival rate, or function (rhythm on EKG), (#viable/#attempted); B is transplant index, or appearance, based on turgor, color, and contractility, ranging from 0–5 (worst to best); hr is time in hours; aprx. is approximately; RL is Ringer's Lactate solution; UW is University of Wisconsin solution; RL+db cAMP is Ringer's Lactate solution to which db cAMP is added, with the concentration values of the added db cAMP indicated in (mM); UW+db cAMP is University of Wisconsin solution to which db cAMP is added, with the concentration values of the added db cAMP indicated in (mM).

DISCUSSION

The data in this heterotopic rat model demonstrate the benefit of the organ preservation or maintenance solution of the subject invention in cardiac preservation, and show that the subject invention is superior to Ringer's Lactate solution and the University of Wisconsin solution. The data in this heterotopic rat model also demonstrate the benefit of db cAMP when this chemical is added to the Ringer's Lactate and the University of Wisconsin solutions, thereby demonstrating that db cAMP is an important, as well as a distinguishing, component of the organ preservation or maintenance solution of the subject invention. However, the data also show that the other ingredients of the subject invention contribute to its effectiveness, since the subject invention is shown to be more effective at preservation times that are substantially longer than the other solutions, whether or not the other solutions contain db cAMP.

In particular, Data in Table I A demonstrate that the organ preservation time of the Ringer's Lactate solution can be extended by adding db cAMP. Data in Table I A show that at four hours of preservation, all grafted hearts remain viable, and both the survival of the graft at ten minutes as well as the transplant index remain high. At eight hours, however, data in Table I A show that only those hearts which were preserved in the Ringer's Lactate solution containing db cAMP have a significant rate of survival, and have high transplant index scores. By twelve hours, data in Table I A show that all of the hearts preserved with the Ringer's Lactate solution are dead and have low transplant index scores; but the hearts preserved in the Ringer's Lactate solution containing db cAMP remain viable.

Data in Table I B likewise demonstrate the beneficial effect of db cAMP in prolonging organ preservation. Data in Table I B demonstrate that organ preservation time of the University of Wisconsin solution can be extended by adding db cAMP. The University of Wisconsin solution is currently thought of as the best preservation solution. Note that experiments involving the UW solution in Table I B use longer preservation times than for those experiments involving the Ringer's Lactate solution in Table I A, because UW solution is a better preservation solution than the Ringer's Lactate solution. Here again, db cAMP enhances cardiac preservation, though by 28 hours, graft survival using the University of Wisconsin solution is decreased, even with db cAMP present in the solution. While the effectiveness of the Columbia University solution is decreased at a preservation time of 36 hours, the Columbia University solution can still be effective.

Data in Table I C demonstrates the effectiveness of the organ preservation or maintenance solution of the subject invention (Columbia University solution) at the longer times of 24, 28, and 36 hours.

Data in Table I D demonstrates the effectiveness of the organ preservation or maintenance solution of the subject invention (Columbia University solution) by comparing it to other test solutions at preservation times of 28 and 36 hours. As mentioned above, the University of Wisconsin solution is currently regarded as the best preservation solution. However, Table I D directly demonstrates that the subject invention is not only superior to the University of Wisconsin solution, but superior even to the University of Wisconsin solution to which db cAMP is added. In other words, it is not the mere presence of db cAMP in the Columbia University solution that explains the superiority of the Columbia University solution over the other organ preservation solutions; the other components of the Columbia University solution also play a role in prolonging organ preservation. Although the relative importance of each component of the Columbia University solution remains to be determined, it can clearly be seen that the organ preservation or maintenance solution of the subject invention is superior to any known preservation solution with respect to prolonged storage of hearts.

Data in Table II show results of transplant experiments using other agents in place of the db cAMP. Db cAMP was chosen because it is an analogue of cAMP which is permeable to the cell membrane. As mentioned above, cyclic AMP (cAMP) is less permeable to the cell membrane than the analogues of cAMP, of which db cAMP is one. The experiment yielding the data in Table II was performed to show that the cyclic AMP portion of the molecule was responsible for its beneficial effects in this transplant model. Data in Table II show results of transplant experiments using another cAMP analogue, 8-bromoadenosine 3-5 cyclic monophosphate, for which similar beneficial results are obtained. However, addition of butyrate alone or bromoadenosine alone had no such beneficial effect. Data in Table II therefore demonstrate that it is the cAMP portion of the db cAMP molecule which is responsible for the beneficial effects with respect to cardiac preservation. Therefore, other suitable analogues of cAMP may be used in the subject invention.

Data in Table III demonstrates the effect of the concentration of db cAMP in Ringer's Lactate and University of Wisconsin solutions. Table III shows that the optimal concentration of db cAMP is at least 2 mM. Not shown are data from additional in vitro experiments which show that concentrations of db cAMP exceeding 4 mM are toxic to endothelial cells. Thus it is not fair to assume that if a little db cAMP is good, a lot is better.

These considerations led to the choice of 2 mMdb cAMP as the optimal concentration to be added to the Columbia University solution.

Experiment One therefore demonstrates that preservation of hearts in a heterotopic rat heart transplant model is improved when db cAMP is added to a simple electrolyte solution (Ringer's Lactate) or to a standard preservation solution (UW solution). Preservation is enhanced still further when the Columbia University organ preservation or maintenance solution is used.

Experiment Two

A preliminary experiment employing materials and methods of Experiment One was performed to evaluate the relative importance of vasodilators.

In this experiment a base solution has the following composition: 67.4 mM D-glucose; 5 mM magnesium sulfate; 25 mM monopotassium phosphate; 95 mM potassium gluconate; and 50 g/l Dextran (molecular weight 308,000 daltons).

The relative importance of nitroglycerin, dibutyryl adenosine 3',5'-cyclic monophosphate (db cAMP), and of adenosine were tested by adding these components individually to the above base solution. Hence, one test solution had 5 mM added to the base solution; the second test solution had 0.1 g/l nitroglycerin added to the base solution; and the third test solution had 2 mM added to the base solution.

RESULTS AND CONCLUSIONS

This is only a preliminary experiment, and the results are recent. However, this experiment has shown that db cAMP and nitroglycerin are important; but that the organ preservation or maintenance solution will function without the presence of adenosine, so long as either db cAMP or nitroglycerin is present. A preferred embodiment, however, contains adenosine.

Further recent experiments suggest that the organ preservation and maintenance solution may function without the presence of db cAMP, so long as the solution contains nitroglycerin. It is believed, however, that the solution may function more effectively with the presence of db cAMP in addition to the nitroglycerin. In particular, in an experiment involving rat hearts which were preserved for twenty four hours, three of three hearts survived in a base solution containing nitroglycerin but not containing db cAMP or adenosine. Hence, the presence of nitroglycerin may be equally important, or perhaps more important, than db cAMP; and the presence of either db cAMP or nitroglycerin is more important than adenosine. It is believed that perhaps nitroglycerin may somehow enter the cell and somehow initiate or influence the making of cAMP by the cells, though the mechanistic or physiological role of nitroglycerin is open to further study.

While it is difficult to measure the relative importance of each individual ingredient in the organ preservation and maintenance solution of the present invention, the presence of vasodilators are very important.

Experiment Three

In Experiment Three, an orthotopic primate heart transplant model is used to demonstrate the effectiveness of the organ preservation or maintenance solution of the subject invention (Columbia University solution).

A (7.4 kg male) baboon was prepared and treated in identical fashion to that done during a human cardiac transplantation, but rather than keeping the heart in an ice bucket for the maximum five (5) hours as is done in human heart transplant procedures, the baboon heart was preserved in the Columbia University solution for about twenty-four (24) hours.

Following a sterile preparation of the chest, the sternum is draped and a median sternotomy performed. The IVC, SVC, and aorta are encircled prior to placing a 16 gauge angiocatheter into the ascending aorta. The SVC is doubly ligated above the sinoatrial node and divided. As the aortic cross-clamp is applied, the IVC is clamped inferiorly and incised as is the left inferior pulmonary vein. These provide a vent for the cardioplegia solution (CU) (about 20 ml/kg) which is now infused at a pressure of about 200 mm Hg (although probably less pressure was seen at the aortic root because of the double length of tubing and the high viscosity of the solution). Following immersion in 700 mL of CU solution (at 0.5 degrees for 23 hours), the heart was again flushed with about 200 mL of freshly prepared CU solution (with the same pressure head) prior to implantation. The recipient baboon was a 9.4 kg female. This animal was also prepped and draped in a sterile fashion and through a median sternotomy, the heart was exposed. A cannulation site was selected in the ascending aorta through which an aortic cannula is inserted. Separate venous cannulae were placed in the SVC and IVC. Once full cardiopulmonary bypass was initiated, the lungs were fixed and the recipient's heart was excised. The donor heart was brought onto the field and anastomoses performed in the following order: left atrial, right atrial, pulmonary artery, and aorta. Air was vented from the heart using a cardioplegia needle and the pulmonary artery. The animal was removed from bypass without difficulty on dopamine, 0.5 mcg/kg/minute. Closure was with a single chest tube and heavy vicryl interrupted sutures. By two (2) hours post-operatively, the chest tube had been removed, the dopamine discontinued, and the animal was awake and moving in its cage. Total preservation time was 23 hours, 45 minutes.

The first baboon received a standard immunosuppressive regimen, including steroids, cyclosporine, and azathioprine. The animal survived and acted normally for four weeks following transplantation, at which time the animal was ethanized and sacrificed to examine the heart, as per experimental protocol.

RESULTS AND DISCUSSION

The recipient baboon survived the surgical heart transplantation procedure in which the heart was preserved for 23 hours, 45 minutes using the organ preservation or maintenance solution of the subject invention (Columbia University solution). This is the first time such extended preservation has ever succeeded in a primate. In contrast, results with UW solution in baboon heart transplant experiments showed that UW solution can not preserve hearts successfully for even eighteen (18) hours; at 18 hours the hearts appear to have decreased function. Attempts at preserving baboon hearts for longer than 18 hours using the University of Wisconsin solution have completely failed with only one of three (3) animals surviving the bypass period of the surgery; however, that animal had severe myocardial damage and died shortly after the operation. With the University of Wisconsin solution, these long term preserved hearts were noted to turn a dark maroon color and become rigid. At 24 hours of attempted preservation with UW solution, hearts showed no evidence of function, and were literally stone dead. We have recently completed our second baboon orthotopic transplantation, and were able to successfully preserve the heart for 24 hours and 15 minutes using the Columbia University solution. These results show that a heart could be preserved for about 24 hours using the Columbia University solution, and function normally following re-implantation. This result is not possible using the University of Wisconsin solution, which is currently considered the best organ preservation solution. This result has never before been achieved in a primate with a simple hypothermic storage of the explanted heart.

In a second baboon experiment, a heart was preserved for 24 hours and 15 minutes. The animal was successfully weaned off bypass, that is, the artificial heart-lung machine that is standard for use in heart surgery. The transplanted heart was able to support the animal's circulation by itself, that is, without mechanical support. The animal lived for fourteen hours, and died of a heart attack. It is believed that the heart preservation procedure was successful, but that the animal died of medical complications that are difficult to manage in an animal intensive care unit.

Although a preferred embodiment of the invention has been described in detail, numerous variations and modifications will readily occur to those skilled in the art. The present invention is not intended to be limited to the preferred embodiment, and its scope is determined by way of the following claims.

Experiment Four

Experiment Four is a preliminary and recent experiment involving a baboon lung transplant.

The composition of the organ preservation and maintenance solution is the same as that used for Experiments One and Three. In this experiment, the transplanted lung was preserved for twenty-two (22) hours. The surgery procedure is similar to that used in other lung transplant procedures. This experiment involved a single lung transplant.

RESULTS AND DISCUSSION

The results show that the organ preservation and maintenance solution of the subject invention was able to preserve the lung for twenty-two hours, following which the baboon had excellent blood oxygenation. The blood oxygenation following the lung transplantation on one hundred percent inspired oxygen was 570 mm Hg, reflecting excellent oxygenation.

This preservation time (twenty-two hours) is far longer than is clinically achievable to date. This result is also impressive because it is generally more difficult to preserve lungs than hearts. This experiment also demonstrates that the organ preservation and maintenance solution can successfully prolong preservation times of other organs besides hearts.

What is claimed is:

1. An aqueous solution for organ preservation or maintenance, comprising:
   a) a vasodilator in an amount sufficient to maintain vascular homeostasis, wherein the vasodilator is selected from the group consisting of:
      adenosine 3',5'-cyclic monophosphate analogues, guanosine 3',5'-cyclic monophosphate analogues, and pertussis toxin;
   b) D-glucose in an amount sufficient to support intracellular function and maintenance of cellular bioenergetics;
   c) magnesium ions in an amount sufficient to support intracellular function and maintenance of cellular bioenergetics;
   d) macromolecules of molecular weight greater than 20,000 daltons in an amount sufficient to maintain endothelial integrity and cellular viability;
   e) potassium ions in a concentration greater than about 110 mM; and
   f) a buffer in an amount sufficient to maintain the average pH of the organ preservation or maintenance solution during the period of organ preservation at about the physiologic pH value.

2. The solution of claim 1, wherein the concentration of D-glucose ranges from about 50 mM to about 80 mM.

3. The solution of claim 1, wherein the concentration of magnesium ions ranges from about 2 mM to about 10 mM.

4. The solution of claim 1, wherein the magnesium ions are selected from the group consisting of magnesium sulfate, magnesium gluconate, and magnesium phosphate compounds.

5. The solution of claim 1, wherein the macromolecules are selected from the group consisting of macromolecules having a molecular weight greater than about 100,000 daltons, a polysaccharide, and a polyethylene glycol.

6. The solution of claim 5, wherein the polysaccharide is a dextran.

7. The solution of claim 6, wherein the dextran is a dextran molecule having a molecular weight of 308,000 daltons.

8. The solution of claim 1, wherein the potassium ions are selected from the group consisting of potassium sulfate, potassium gluconate, and monopotassium phosphate ($KH_2PO_4$) compounds.

9. The solution of claim 1, wherein the concentration of potassium ions ranges from about 110 mM to about 140 mM.

10. The solution of claim 1, wherein the buffer is monopotassium phosphate ($KH_2PO_4$).

11. The solution of claim 1, further comprising impermeant anions in an amount sufficient to maintain endothelial integrity and cellular viability.

12. The solution of claim 11, wherein the impermeant anions are selected from the group consisting of gluconate anions and lactobionate anions.

13. The solution of claim 12, wherein the impermeant anions are gluconate anions having a concentration that ranges from about 85 mM to about 105 mM.

14. The solution of claim 12, wherein the impermeant anions are gluconate anions which are selected from the group consisting of potassium gluconate and magnesium gluconate compounds.

15. The solution of claim 1, further comprising an anticoagulant in an amount sufficient to prevent clotting of blood within the capillary bed of the organ.

16. The solution of claim 15, wherein the anticoagulant is selected from the group consisting of heparin and hirudin.

17. The solution of claim 16, wherein the anticoagulant is heparin having a concentration that ranges from about 1000 units/l to about 100,000 units/l.

18. The solution of claim 1, further comprising an antioxidant in an amount sufficient to decrease reperfusion injury secondary to oxygen free radicals.

19. The solution of claim 18, wherein the antioxidant is selected from the group consisting of butylated hydroxyanisole (BHA), butylated hydroxytoluene (BHT), Vitamin C, and Vitamin E.

20. The solution of claim 19, wherein the antioxidant is butylated hydroxyanisole (BHA) at a concentration range from about 25 microM to about 100 microM.

21. The solution of claim 20, further comprising butylated hydroxytoluene (BHT) at a concentration range from about 25 microM to about 100 microM.

22. The solution of claim 1, further comprising a reducing agent in an amount sufficient to decrease reperfusion injury secondary to oxygen free radicals.

23. The solution of claim 1, further comprising N-acetylcysteine in an amount sufficient for cells to produce glutathione.

24. The solution of claim 23, wherein the concentration of N-acetylcysteine ranges from about 0.1 mM to about 5 mM.

25. The solution of claim 1, further comprising an agent that prevents calcium entry into cells in an amount sufficient to prevent calcium entry into cells.

26. The solution of claim 25, wherein the agent that prevents calcium entry into cells is verapamil.

27. The solution of claim 26, wherein the concentration of verapamil ranges from about 2 microM to about 25 microM.

28. The solution of claim 1, further comprising a bacteriostat in an amount sufficient to inhibit bacterial growth.

29. The solution of claim 28, wherein the bacteriostat is selected from the group consisting of cefazolin and penicillin.

30. The solution of claim 29, wherein the bacteriostat is cefazolin having a concentration that ranges from about 0.25 g/l to about 1 g/l.

31. The solution of claim 1, wherein the osmolarity ranges from about 315 mOSm/l to about 340 mOSm/l.

32. A method of preserving or maintaining an organ, comprising contacting the organ with the solution of claim 1.

33. The method of claim 32, wherein the contacting comprises immersion, infusion, flushing, or perfusion.

34. The method of claim 32, wherein the organ is an organ intended for transplantation.

35. The method of claim 32, wherein the organ is a heart.

36. The method of claim 35, wherein the heart is involved in cardiac surgery.

37. The solution of claim 1, wherein the vasodilator is dibutyryl adenosine 3',5'-cyclic monophosphate (db cAMP).

38. The solution of claim 37, wherein the concentration of dibutyryl adenosine 3',5'-cyclic monophosphate (db cAMP) ranges from about 1 mM to about 4 mM.

39. The method of claim 32, wherein the organ is a lung.

40. The solution of claim 1, further comprising adenosine.

41. The solution of claim 40 wherein the concentration of adenosine ranges from about 3 mM to about 20 mM.

42. The solution of claim 1, further comprising nitroglycerin.

43. The solution of claim 42 wherein the concentration of nitroglycerin ranges from about 0.05 grams per liter to about 0.2 grams per liter.

* * * * *